United States Patent
Dhawan

(10) Patent No.: US 10,653,343 B2
(45) Date of Patent: May 19, 2020

(54) SYSTEM AND METHOD FOR NON-INVASIVE GLUCOSE MONITORING USING NEAR INFRARED SPECTROSCOPY

(71) Applicant: NEW JERSEY INSTITUTE OF TECHNOLOGY, Newark, NJ (US)

(72) Inventor: Atam Dhawan, Randolph, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 345 days.

(21) Appl. No.: 14/042,517

(22) Filed: Sep. 30, 2013

(65) Prior Publication Data

US 2017/0105663 A1 Apr. 20, 2017
US 2018/0000390 A9 Jan. 4, 2018

Related U.S. Application Data

(60) Provisional application No. 61/706,384, filed on Sep. 27, 2012.

(51) Int. Cl.
*A61B 5/00* (2006.01)
*A61B 5/145* (2006.01)
(Continued)

(52) U.S. Cl.
CPC ........ *A61B 5/14532* (2013.01); *A61B 5/0075* (2013.01); *A61B 5/1455* (2013.01);
(Continued)

(58) Field of Classification Search
CPC . A61B 5/14532; A61B 5/0075; A61B 5/6816; A61B 5/1455; A61B 5/14546; A61B 5/02438; A61B 5/14551
See application file for complete search history.

(56) References Cited

U.S. PATENT DOCUMENTS 5,137,023 A * 8/1992 Mendelson ........ A61B 5/14532
600/316
5,355,880 A * 10/1994 Thomas ............. A61B 5/02007
128/925

(Continued)

OTHER PUBLICATIONS

D'Alessandro, Brian, and Atam P. Dhawan. "Depth-dependent hemoglobin analysis from multispectral transillumination images." IEEE Transactions on Biomedical Engineering 57.10 (2010): 2568-2571.*

(Continued)

*Primary Examiner* — Navin Natnithithadha
*Assistant Examiner* — Andrey Shostak
(74) *Attorney, Agent, or Firm* — McCarter & English, LLP

(57) ABSTRACT

A method for noninvasively measuring blood concentration of a substance, such as, for example, blood glucose levels, is described herein. The method may comprise measuring an initial absorption data using near infrared spectroscopy (NIR), and obtaining a second set of absorption data. The initial absorption data, along with the second set of absorption data, may then be adjusted by applying a convolution function and a Monte Carlo simulation to the raw data. In a step, an initial estimate of the level of the substance in the blood, such as, for example, initial blood glucose level, may be calculated based on the adjusted data and pulse oximetry information using a mixing model equation.

21 Claims, 20 Drawing Sheets

(51) Int. Cl.
    *A61B 5/1455*    (2006.01)
    *A61B 5/024*     (2006.01)
(52) U.S. Cl.
    CPC ........ *A61B 5/14546* (2013.01); *A61B 5/6816* (2013.01); *A61B 5/02438* (2013.01); *A61B 5/14551* (2013.01)

(56) References Cited

U.S. PATENT DOCUMENTS

| | | | | |
|---|---|---|---|---|
| 2003/0023152 | A1* | 1/2003 | Abbink | A61B 5/0075 600/316 |
| 2006/0276696 | A1* | 12/2006 | Schurman | A61B 5/0066 600/316 |
| 2010/0042004 | A1* | 2/2010 | Dhawan | A61B 5/0059 600/476 |
| 2011/0029247 | A1* | 2/2011 | Kalathil | A61B 5/14551 702/19 |
| 2013/0296668 | A1* | 11/2013 | Kalathil | A61B 5/14551 600/323 |

OTHER PUBLICATIONS

Atam P. Dhawan, et al., "Optical Imaging Modalities for Biomedical Applications", IEEE Transactions on Reviews in Biomedical Engineering, vol. 3(1), pp. 69-92, 2010.

Brian D'Alessandro, et al., Depth-Dependent Hemoglobin Analysis from Multispectral Transillumination Images, IEEE Transactions on Biomedical Engineering Special Issue on Multi-Parameter Optical Imaging and Image Analysis, vol. 57(10), pp. 2568-2571, 2010.

Burmeister, et al. "Spectroscopic Considerations for Noninvasive Blood Glucose Measurements with Near Infrared Spectroscopy." LEOS Newsletter. IEEE Lasers and Electro-Optics Society. Web. Mar. 30, 2011. <http://www.ieee.org/organizations/pubs/newsletters/leos/apr98/infrared.htm>.

K. Maruo, et al., "In Vivo Noninvasive Measurement of Blood Glucose by Near-Infrared Diffuse-Reflectance Spectroscopy," Appl. Spectrosc. 57, 1236-1244 (2003).

Khalil, Omar S. "Spectroscopic and Clinical Aspects of Noninvasive Glucose Measurements." Clinical Chemistry 45 (1992): 165-77. Clinical Chemistry. American Association for Clinical Chemistry, Inc, 1999. Web. Mar. 30, 2011. <http://www.clinchem.org/cgi/content/abstract/45/2/165>.

L. Davis, Handbook of Genetic Algorithms. New York: Van Nostrand Reinhold, Table of Contents and pp. 1-22 and 314-323, 1991.

L. Wang, et al., "MCML—Monte Carlo Modeling of Light Transport in Multi-Layered Tissues," Computer Methods and Programs in Biomedicine, vol. 47, No. 2, pp. 131-146, 1995.

Waynant, R. W. et al., "Overview of Non-Invasive Optical Glucose Monitoring Techniques." LEOS Newsletter. IEEE Lasers and Electro-Optics Society. Web. Mar. 30, 2011. <http://www.ieee.org/organizations/pubs/newsletters/leos/apr98/overview.htm>.

* cited by examiner (a) 600 nm (b) 680 nm (c) 780 nm (d) 800 nm (e) 875 nm

| Parameter | Estimated Value Wavelength Set-1 | Estimated Value Wavelength Set-2 |
|---|---|---|
| $C_M$ | 1.11% | 1.08% |
| $C_B$ | 24.17% | 28.25% |
| [Glucose] | 134.3% | 119.6% |

True values: $C_M = 1\%$, $C_B = 30\%$, and [Glucose] = 100%.

FIG. 10

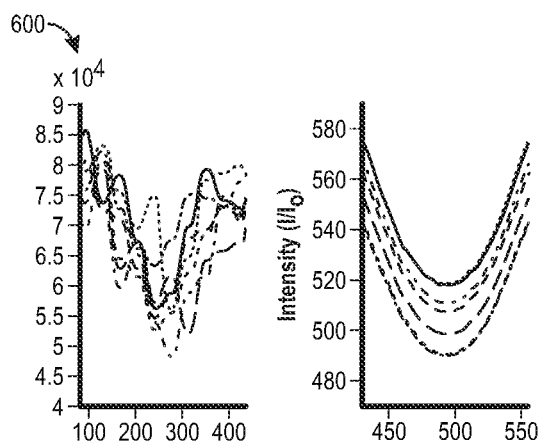
FIG. 15A
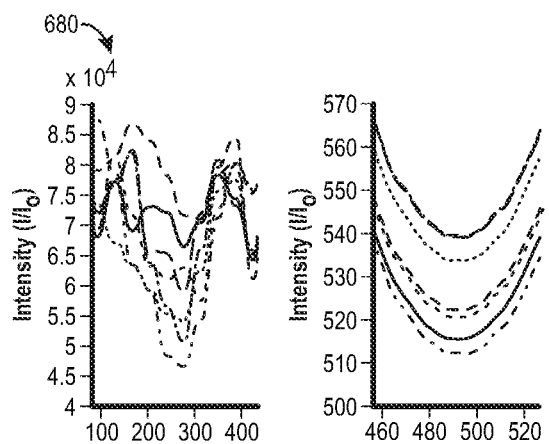
FIG. 15B
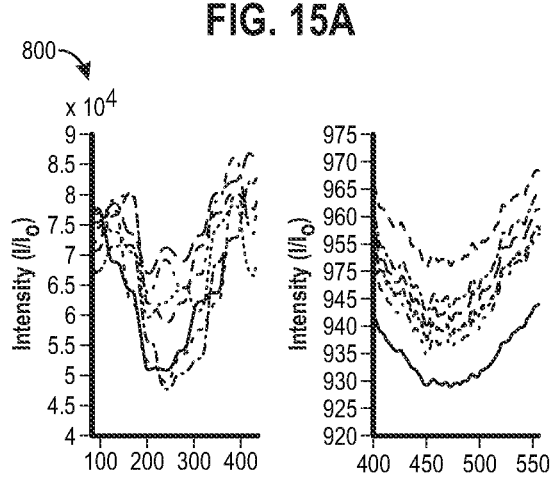
FIG. 15C
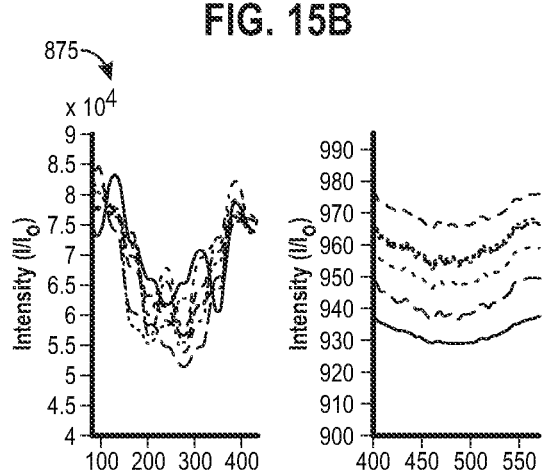
FIG. 15D
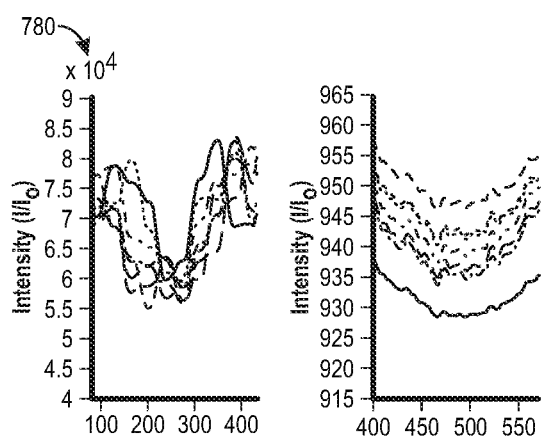
FIG. 15E
FIG. 15F

SYSTEM AND METHOD FOR NON-INVASIVE GLUCOSE MONITORING USING NEAR INFRARED SPECTROSCOPY

CROSS-REFERENCE TO RELATED APPLICATION

This application claims the benefit of U.S. Provisional Patent Application No. 61/706,384, filed on Sep. 27, 2012. The entire content of the foregoing provisional patent application is herein incorporated by reference.

FIELD OF THE INVENTION

This invention relates to a method of monitoring of diabetes, more specifically it relates to blood glucose monitoring. It also relates to the apparatus used in the method. The principle of the invention can also be sued to monitor other substances circulating in the blood, such as glycolated hemoglobin and cholesterol.

BACKGROUND OF THE INVENTION

Diabetes mellitus is a chronic disease currently affecting about one third of the US population including those in the pre diabetic stage. Clinical management of both Type-1 and Type-2 diabetes relies on accurate monitoring of blood glucose concentrations at least once a day. Current devices rely on enzyme oxidation analyses, which require a prick of blood every time glucose levels are checked. This invasive method of glucose monitoring causes pain and tissue-sensitivity to users making it difficult to have repeated measurements causing failure in compliance, especially for chronic patients.

26 million people in the US are affected by diabetes while 79 million in the pre-diabetic stage. Worldwide, the number swells to 285 million adults. Further, 3.8 million deaths are caused by diabetes related diseases in the world annually. Patients who are required to use traditional glucose monitoring methods are often faced with pain and increased sensitivity in their fingertips.

SUMMARY OF THE INVENTION

The present invention relates to techniques for non-invasive blood glucose measurements via imaging. It is based on the observation that there is a distinction between the substance to be measured and water that can be measured via multispectral near-infrared spectroscopy (NIR).

Thus, the present invention allows for an initial absorption measurement at a continuous or relatively high sampling rate at discrete wavelengths somewhere within the range of 600 nm to about 1000 nm over a sufficient period of time so as to be able to analyze any temporal variations while also providing time tag information for systolic and diastolic events. This information along with pulse oximetry information taken at this time is used to help estimate actual blood concentration. After this initial absorption data information has been taken another round of absorption data is taken at a lower sampling rate utilizing at least one wavelength within the about 600 nm to about 1000 nm range. This raw data is collected at least at the time tag points related to systolic and diastolic events, but greater collection of data points is also embraced. This raw data is corrected via a convolution function while also utilizing a Monte Carlo simulation and, along with pulse oximetry information, a mixing model equation to provide initial estimate of blood concentration. The estimate is further optimized by genetic algorithm for a final blood substance reading.

The invention also relates to an apparatus specifically designed to carry out the method of the invention. The apparatus includes a means of illuminating a place on a patient's body where the measurement can be made and a means for measuring the amount of absorption of the illumination. The apparatus also includes a means for the data to be recorded and analyzed and then transformed into a meaningful result. The apparatus further includes a means to report its results as well as a communication ability to other devices.

BRIEF DESCRIPTION OF THE DRAWINGS

So that those having ordinary skill in the art will have a better understanding of how to make and use the disclosed gel blends, reference is made to the accompanying figures wherein:

FIG. 10 depicts an estimation of un-mixing results;

FIGS. 15A-15F show absorption measurements across the simulated phantom and imaged physical tube phantom for various levels of glucose concentration at different wavelengths.

DETAILED DESCRIPTION OF INVENTION

Figure 1A:
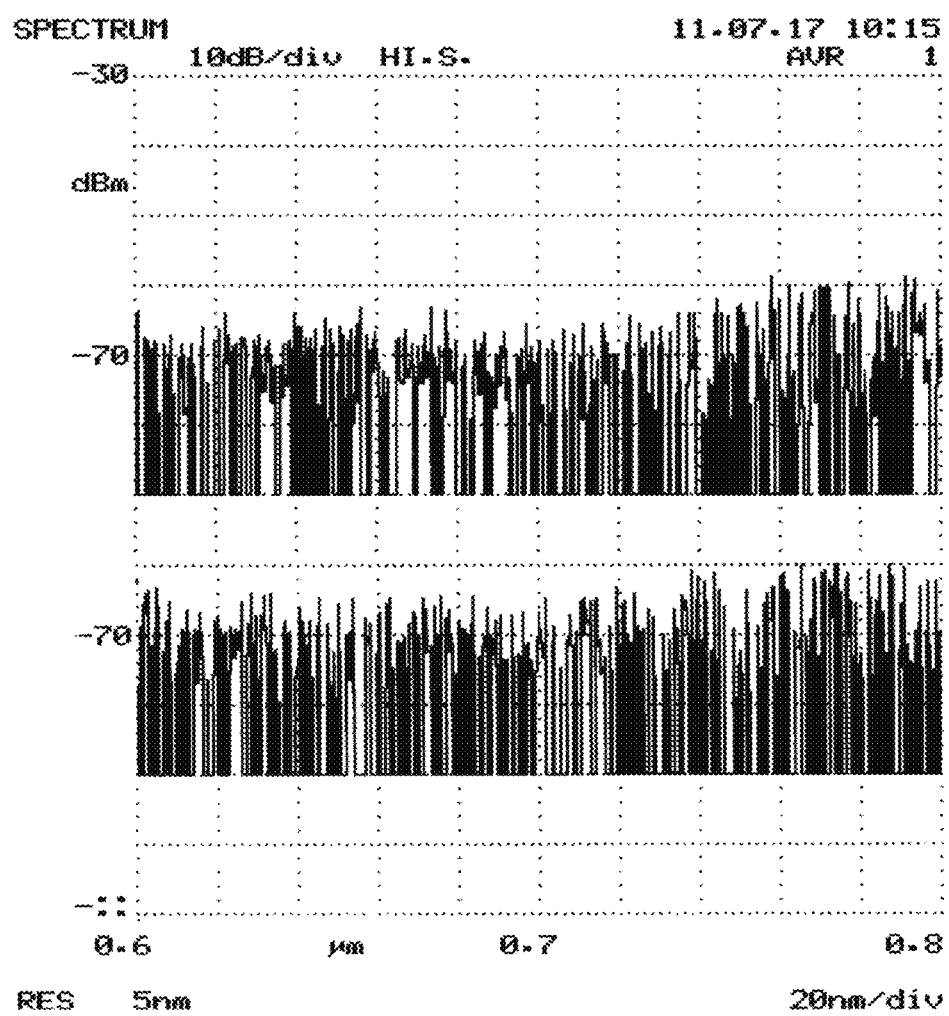
FIGS. 1A-1F show comparisons for glucose and water.
Figure 1B:
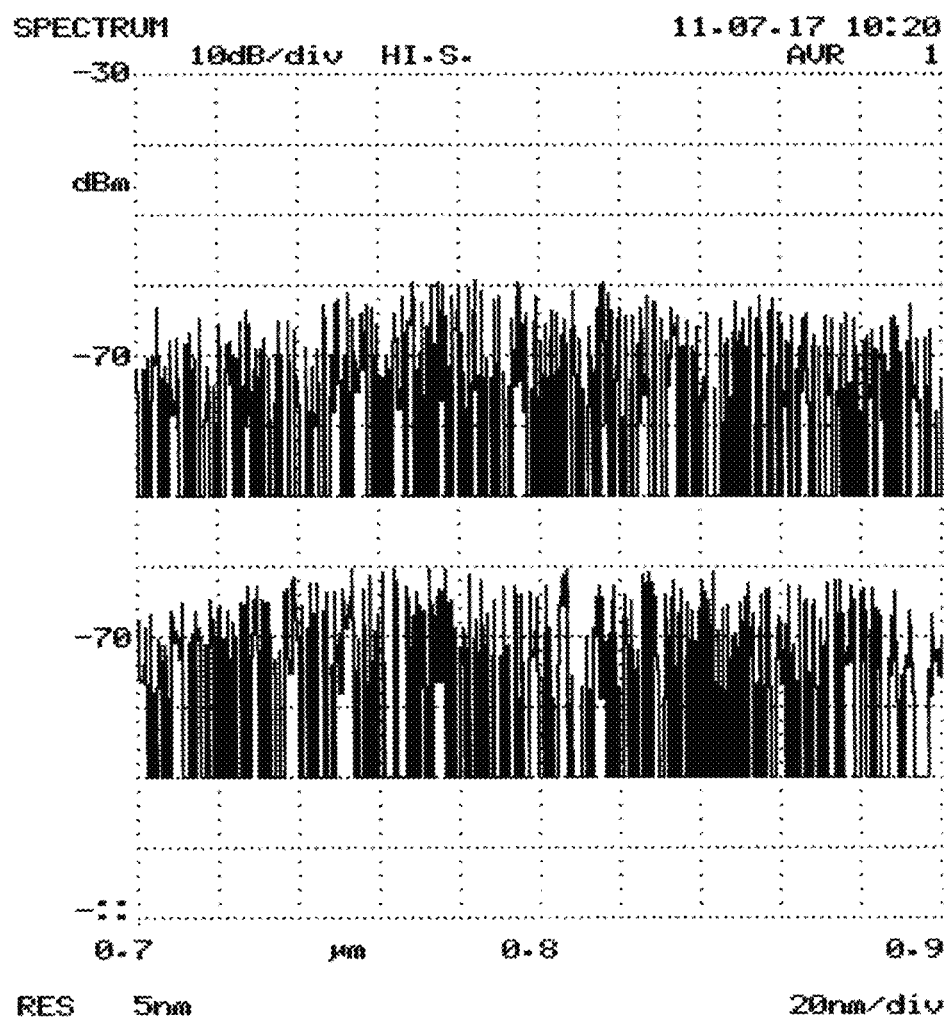
Figure 1C:
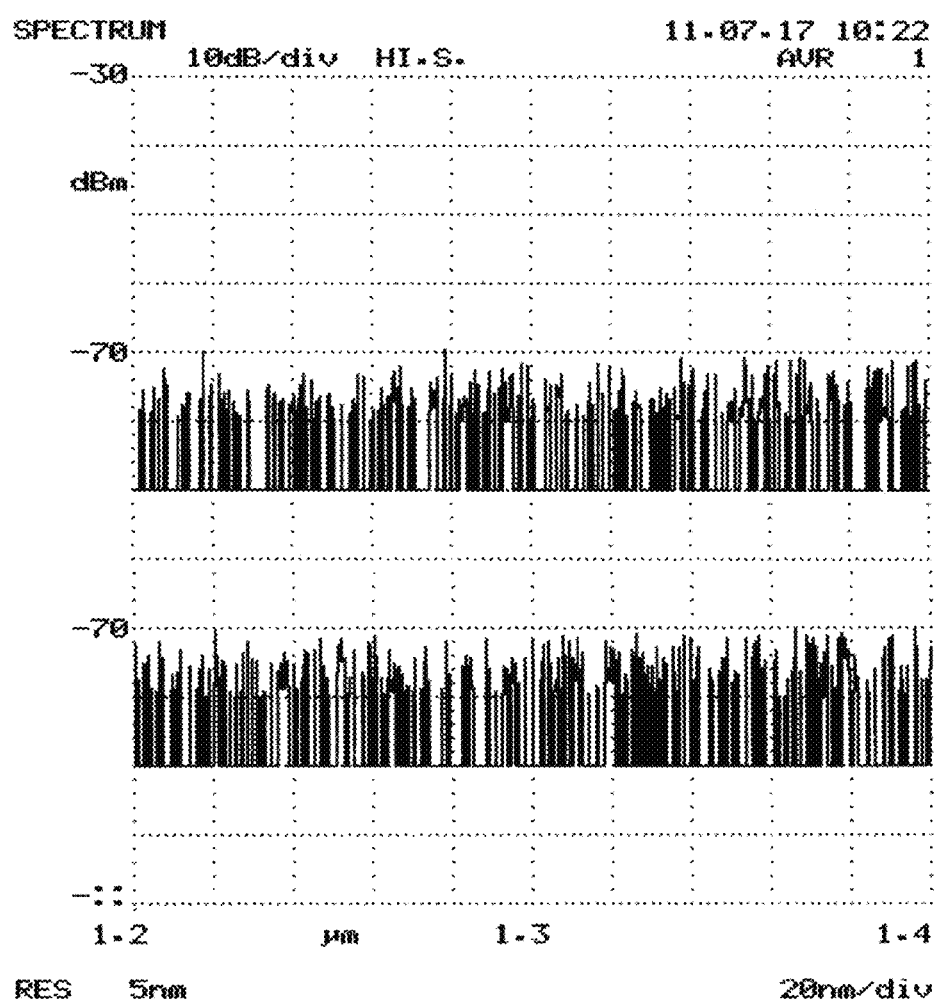
Figure 1D:
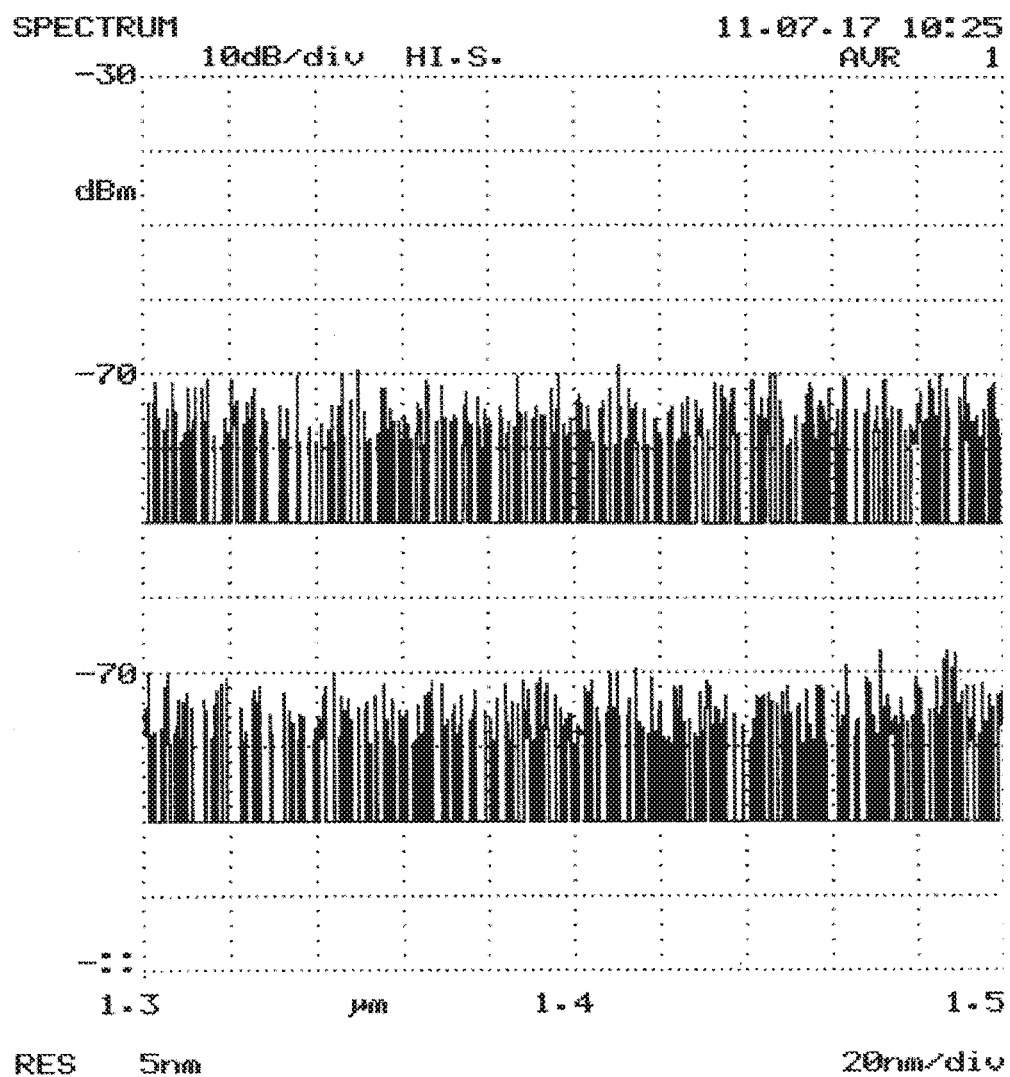
Figure 1E:
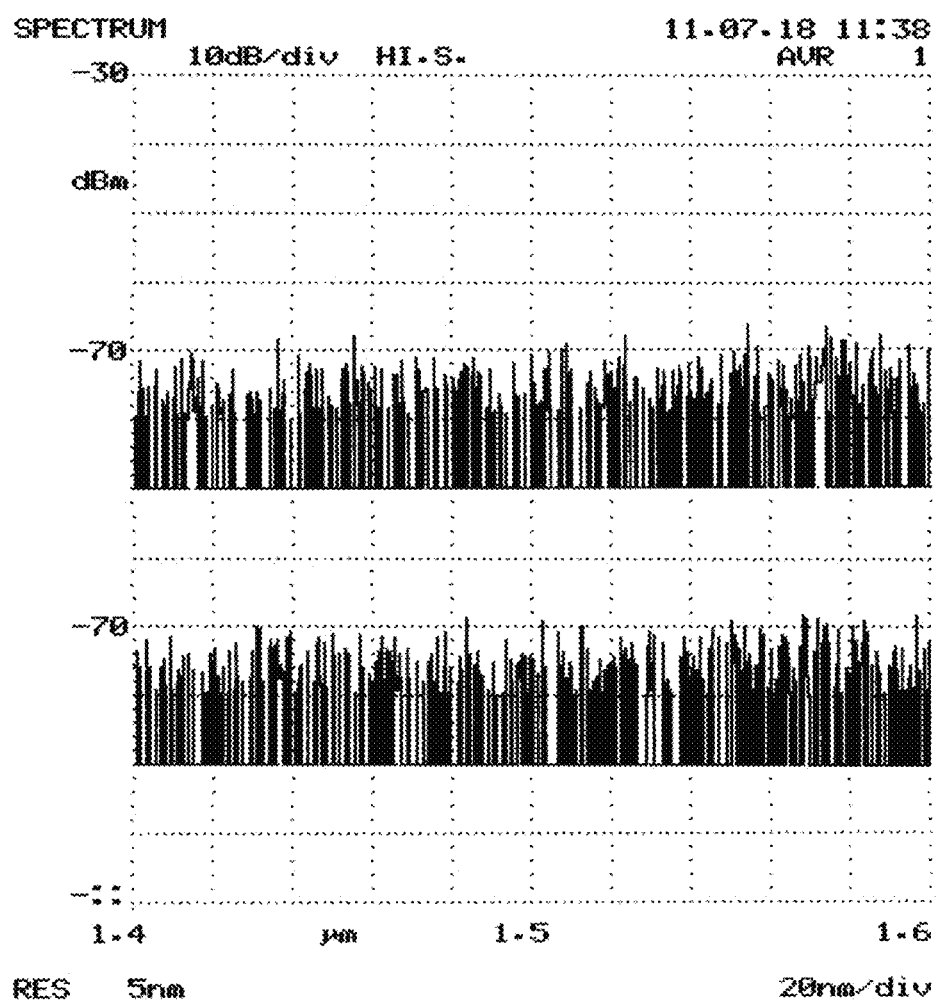
Figure 1F:
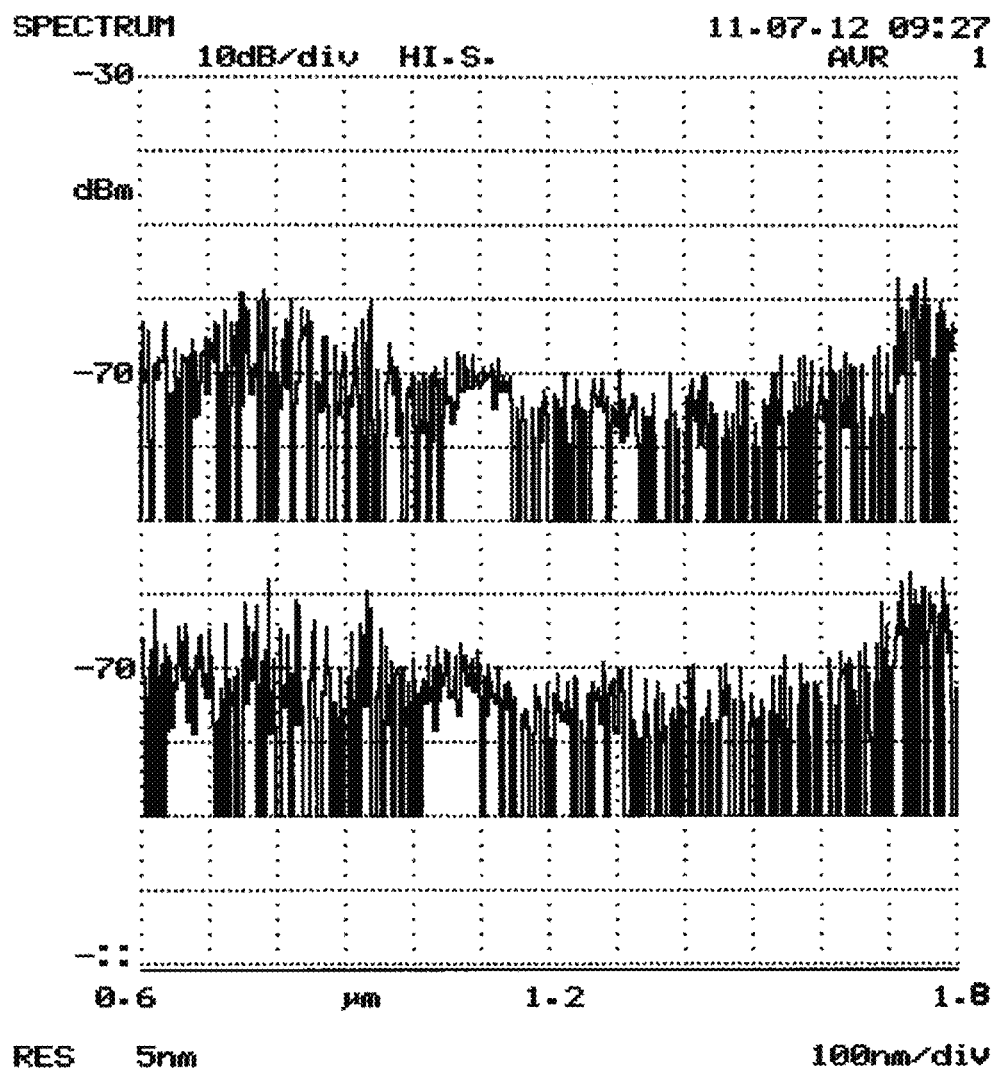

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

More particularly, the invention relates to a method of monitoring blood concentration of a substance which comprises measuring a initial absorption data using near infrared spectroscopy (NIR), obtaining a second set of absorption data, adjusting the data using a convolution function and a Monte Carlo simulation, and using a mixing model equation along with pulse oximetry information and the adjusted data to provide an initial estimate of the level of the desired substance.

In a particular embodiment of the invention, the method is non-invasive to a patient whose blood is being analyzed.

The substance to be measured can be any substance which has an observable difference with water at the wavelengths at which the measurements are taken. Non-limiting examples include glucose, glycolated hemoglobin or cholesterol.

The initial absorption is measured over a sufficient period of time to analyze possible temporal variations while also providing time tag information for systolic and diastolic events. The initial estimate of the level of the desired substance is optimized by genetic algorithm to obtain a final blood reading.

Another embodiment of the invention relates to a method of monitoring blood concentration of glucose which comprises measuring a initial absorption data using near infrared spectroscopy (NIR), obtaining a second set of absorption data, adjusting the data using a convolution function and a Monte Carlo simulation, using a mixing model equation along with pulse oximetry information and the adjusted data to provide an initial estimate of the level of glucose.

Another embodiment of the invention relates to a method as described above which is non-invasive to a patient whose blood is being analyzed. The initial absorption can be measured over a sufficient period of time to analyze possible temporal variations while also providing time tag information for systolic and diastolic events. The initial estimate of the level of glucose can be optimized by genetic algorithm to obtain a final blood glucose reading.

Yet another embodiment of the invention relates to an apparatus for obtaining a non-invasive measurement of a substance in the blood which comprises, a NIR light source, a detector to determine absorption, a computer to analyze and transform data a power source, an archive, a communication system, and a user interface. In some embodiments the apparatus has at least one component of the apparatus can be placed on the skin. A non-limiting example is the ear lobe.

In certain embodiments of the present invention illumination is carried out in the optical and NIR range of about 600 nm-about 1200 nm. In certain embodiments of the present invention pulse mode measurement can be utilized wherein instead of collecting data at regular sampling rate, the data can be collected at specific times related to desired events and/or averaged out over a time period. For example, the absorption data can be first collected at 600 and 910 nm to measure heart rate and related events such systolic and diastolic events at higher sampling rates. Once the heart rate events are established, subsequent data is collected at these time intervals through appropriate programming of the sample, hold and analog-to-digital convertor of the data acquisition system/chip.

In certain embodiments of the present invention data is collected at specific times such as systolic and diastolic events of the heart cycle. The data acquisition system is synchronized with these events.

In certain embodiments of the present invent surface are of the tissue that is illuminated has an about 1 cm diameter maximum value. This refers to the surface area of the tissue that is illuminated by a source or multiples of sources that illuminates the tissue with specific visible optical and NIR beam(s) to produce images and measurements of absorption data from detectors using either transmittance or transillumination methods as defined above.

In certain embodiments of the present invention the glucose measurement range is about 3 mmol/L-about 10 mmol/L or about 50 mg/dL-about 150 mg/dL (calibrated with standard scale 50-500 pmol/L) with accuracy within 10%; and sensitivity >90%.

Certain embodiments of the present invention utilize a low-power consumption subsystem design.

Certain embodiments of the present invention utilize Li-Polymer battery with battery charging and power management.

Certain embodiments of the present invention utilize Micro-USB connectivity for battery charging.

In certain exemplary embodiments of the present invention blood glucose measurement takes place on any skin surface of individual. In a further embodiment the present invention is affixed to the ear lobe to effectuate the measurements.

In certain exemplary embodiments of the present invention the measurement device of the interacts wirelessly with a receiving device to receive and record measurements and interface with patient and/or care provider. The list of wireless devices includes but is not limited to, smart phone devices, laptop computers, tablets, and stand alone wireless device developed solely for the present invention.

Certain embodiments of the present invention utilize system integration with standard components such as data sampling/acquisition chips with signal multiplexers and analog to digital converters, and portable processors/computers as well as control and processing/estimation algorithms on portable processors/computers.

Certain embodiments of the present invention perform local computation and processing as well as storage and wireless communication/networking via applications for smart phone or computing device.

Early work related to the present invention stems from finding a distinction between glucose and water that could be measured via multispectral near-infrared spectroscopy (NIR). In order to begin addressing this, spectra of water and glucose solutions were taken using an optical spectrum analyzer. Using the data from the spectrum, specific wavelengths were targeted for the analysis of absorption coefficients at respective wavelengths. Preliminary data confirms that this method is viable as absorption coefficients vs. wavelength in the NIR show a significant distinction, as depicted in FIGS. 1A-1F.

The following equations are exemplary of further mathematical analysis of some of the optical properties of skin yields, according to aspects of the present disclosure. For example, various absorption coefficients (e.g., $\mu_a$) at a specific wavelength (e.g., $\lambda$) may be calculated for various chromophores found within tissue (e.g., melanin, epidermis, dermis, blood), including a baseline absorption coefficient for reference. The equations below may be employed to estimate specific information about depth of structures and/or chromophores disposed in tissue (e.g., human skin).

$$\mu_a^{baseline}(\lambda) = 0.244 + 85.3e^{\frac{-(\lambda-154)}{66.2}} [cm^{-1}]$$

$$\mu_a^{melanin}(\lambda) = 6.6 \times 10^{11}(\lambda^{-3.33})$$

-continued $$\mu_a^{epidermis}(\lambda) = C^{melanin}\mu_a^{melanin}(\lambda) + (1 - C^{melanin})\mu_a^{baseline}(\lambda)$$

$$\mu_a^{dermis}(\lambda) = C^{blood}\mu_a^{blood}(\lambda) + (1 - C^{blood})\mu_a^{baseline}(\lambda)$$

$$\mu_a^{blood}(\lambda) = ([SO_2])\mu_a^{HbO_2}(\lambda) + (1 - [SO_2])\mu_a^{Hb}(\lambda)$$

where
- $\mu_a$ (absorption coefficient)
- $\mu_s$ (scattering coefficient)
- $HbO_2$ (oxygenated hemoglobin)
- $Hb$ (deoxygenated hemoglobin)
- $SO_2$ (blood oxygen saturation)
- g (anisotropy factor)
- n (refraction index).

The equations described immediately above are modeled for measurements of absorption coefficients related to specific chromophores such as (deoxy)hemoglobin ($H_b$), oxygenated hemoglobin ($H_bO_2$) in the blood in a tissue that is imaged, for example, through a direct transmittance or a transillumination method. In a direct transmittance method, the tissue is illuminated by a visible light or NIR source at specific wavelength(s) in the perpendicular direction to the surface of the tissue from one side, transmitted through the tissue, and collected on the other side by a single and/or a plurality of detectors that measure the intensity of the transmitted beam to determine absorption data at the specific location of the tissue. The location is specified by a pixel in the overall image that is produced by repeating the above process at different locations (pixels) for further processing and analysis to estimate concentration of specific chromophores in the tissue. Certain embodiments of the present invention utilize the direct transmittance method.

In a further mode of illumination referred to herein as transillumination, the visible light and NIR beam at specific wavelength(s) is directed at about an 45 degree angle to the surface of the tissue and a backscattered diffused beam is collected by the detectors on the same side of the tissue to form the image. Certain embodiments of the present invention utilize the transillumination method.

Transillumination and direct transmittance are not the only illumination methods embraced by the present invention and are discussed for illustrative purposes only. Any other illumination process that is known to one skilled in the art is embraced by the present invention.

Figure 2:
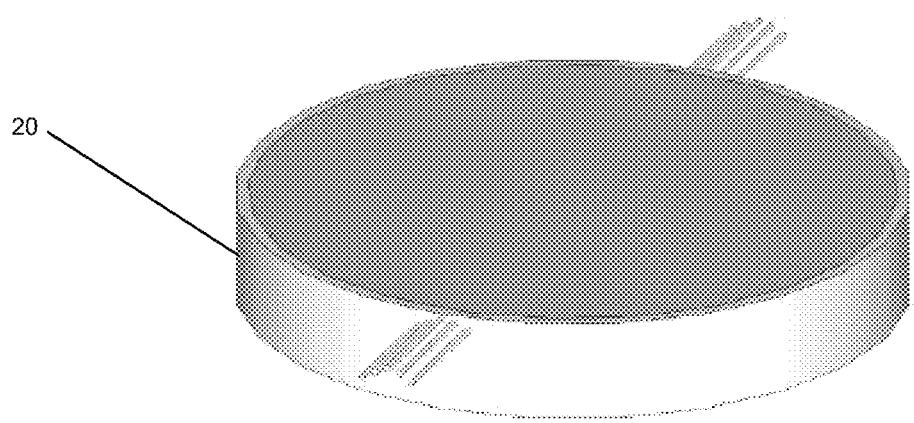
FIG. 2 illustrates a skin phantom for transillumination imaging.

For illustrative purposes only, transillumination absorption tests are often done with an illumination ring 28 placed over a skin phantom 20 (FIG. 2), however any other standard transillumination protocol known to one skilled in the art is embraced by the present invention.

Figure 3:
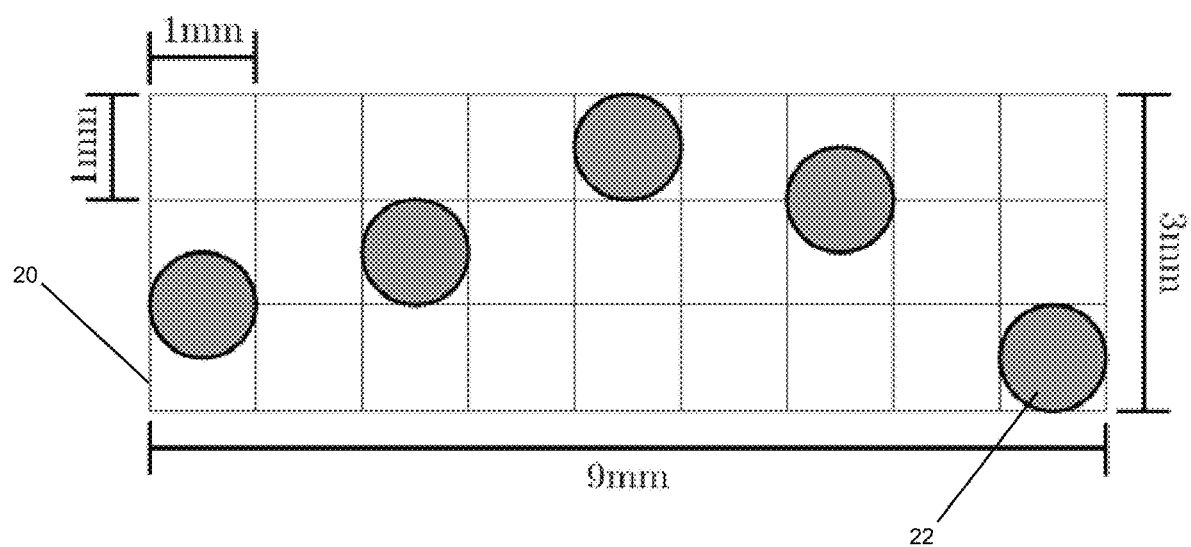
FIG. 3 displays cross-section of a skin phantom showing location of capillary tubes.
Figure 4A:
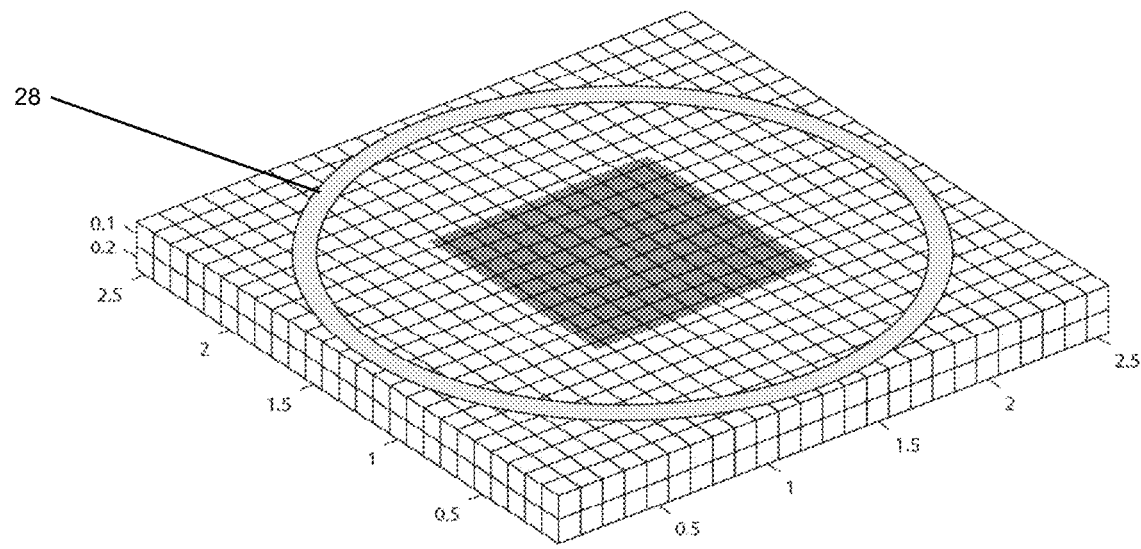
FIG. 4A illustrates an experimental set-up for Monte Carlo simulation.
Figure 4B:
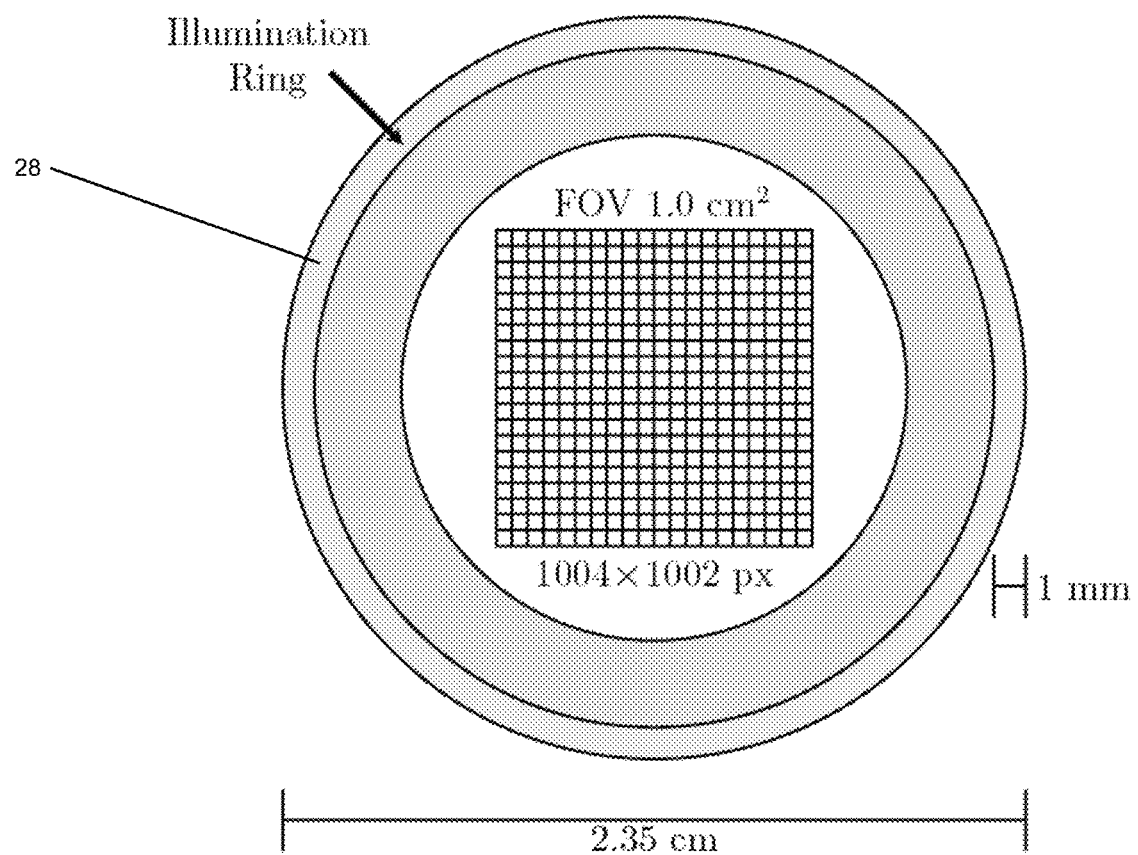
FIG. 4B illustrates a corrected transillumination imaging apparatus.
Figure 5:
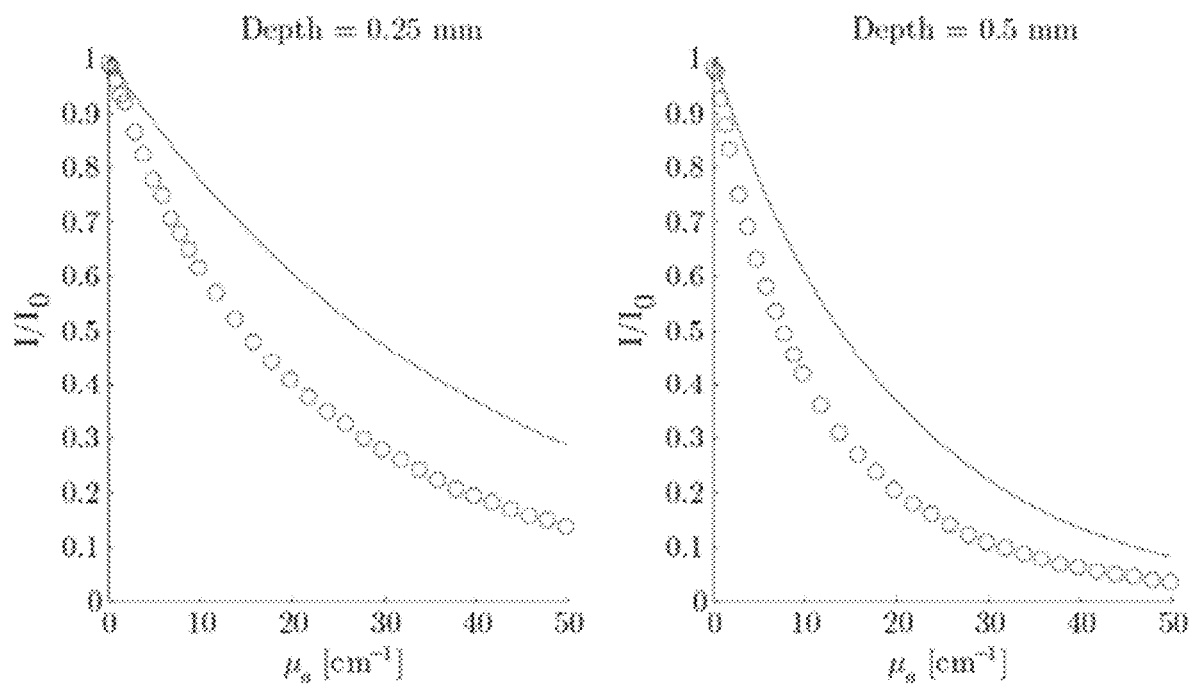
FIG. 5 shows intensity to $\mu_a$ relation performance when applying Beer's Law.
Figure 6:
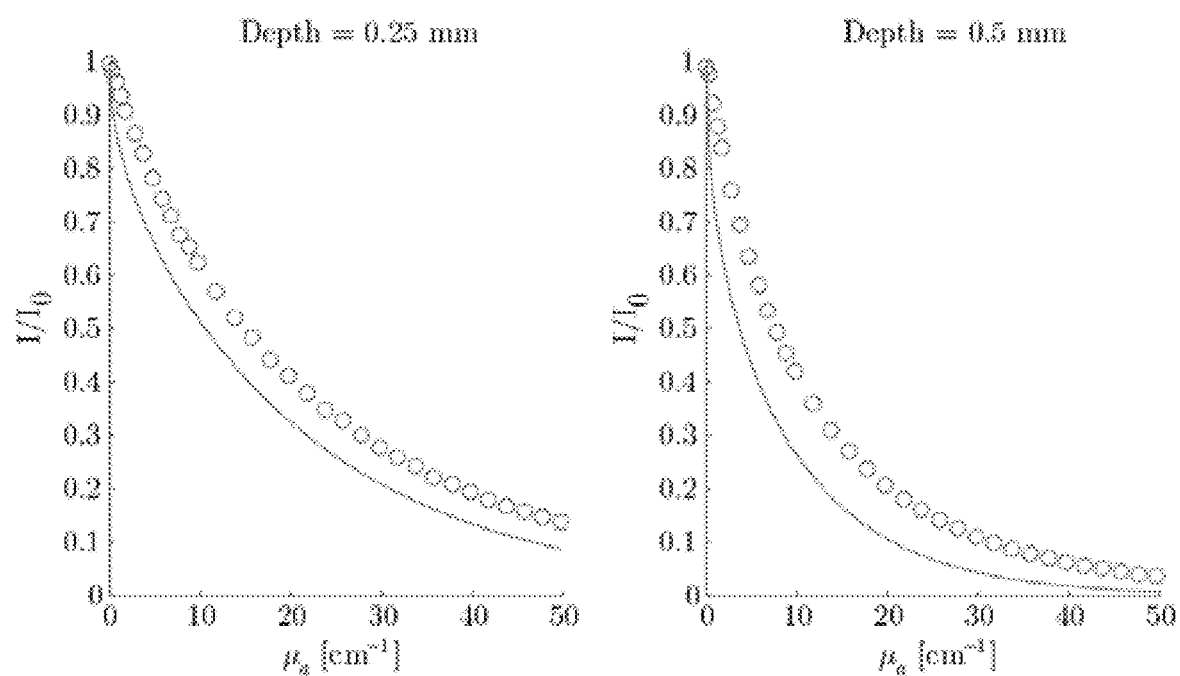
FIG. 6 shows intensity to $\mu_a$ relation performance when applying $\mu_{\text{eff}}$ equation.
Figure 7:
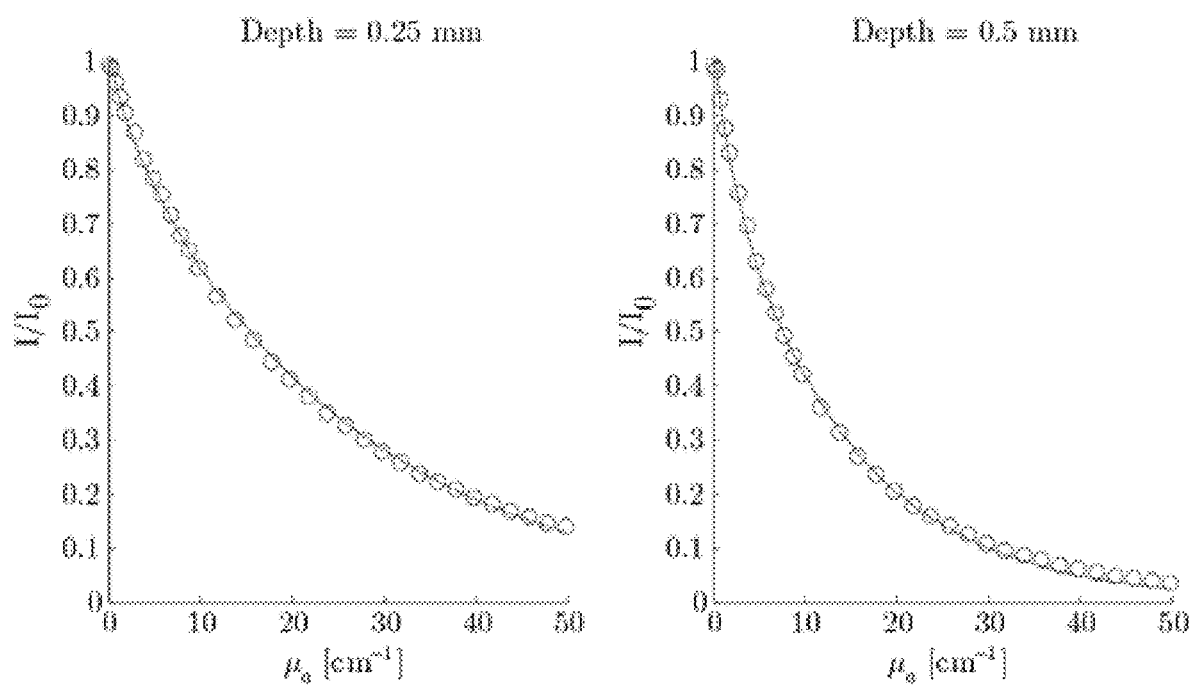
FIG. 7 shows intensity to $\mu_a$ relation performance when applying nevoscope corrected equation.
Figure 8:
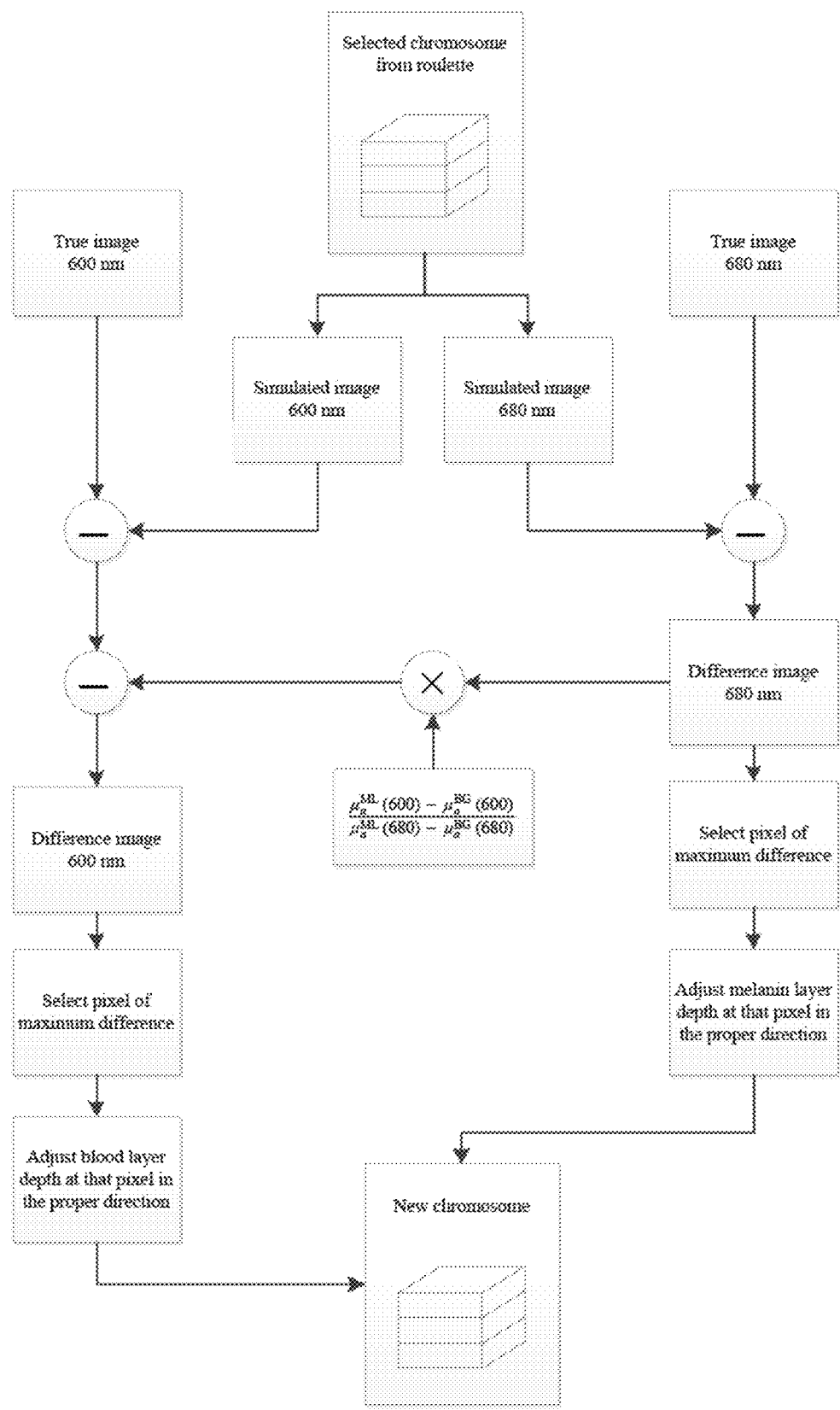
FIG. 8 shows a schematic of one embodiment of the present invention as it optimizes the system utilizing genetic algorithm.

One example of a transillumination test utilizes a particular phantom with 5 embedded capillary tubes 22 (FIG. 3) spaced at 0.5 mm depth increments and the tubes can be filled with artificial $HbO_2$ or $Hb$ (FIG. 3). Transillumination imaging for the example can be seen in FIGS. 4A and 4B. For each simulation utilizing this example a random position in the ring 28 is selected for entrance to voxel grid at a 45 degree angle, as seen in FIGS. 4A and 4B, and as described by the following exemplary equations:

$$x = \sqrt{(r_2^2 - r_1^2)\xi_1 + r_1^2}\cos(2\pi\xi_2)$$

$$y = \sqrt{(r_2^2 - r_1^2)\xi_1 + r_1^2}\sin(2\pi\xi_2)$$

-continued $$dx = -\frac{\sqrt{2}}{2}\cos(2\pi\xi_2)$$

$$dy = -\frac{\sqrt{2}}{2}\sin(2\pi\xi_2)$$

$$dz = \frac{\sqrt{2}}{2}$$

Where x and y correspond to voxel information relating to the image of the structure deep within skin tissue.

Intensity to absorption coefficient $\mu_a$ relation is modeled for chromophore separation through the inverse equation:

$$\mu_a = f^{-1}(I, I/I_0)$$

Where I is a pixel intensity value in an image of the tissue with the chromophore such as oxygen or glucose, $I_0$ is the intensity from the tissue without the chromophore, $\mu_a$ is absorption coefficient of the chromophore, and f is the depth of the location of the chromophore in the tissue. The results of this chromophore correction test can be seen in FIGS. 5-8. Certain embodiments of the present invention use the measurement protocol described above to achieve glucose concentration measurements in the blood of test subjects.

In certain embodiments of the present invention, a Monte Carlo simulation of the tissue and imaging method is used in tandem with the multispectral NIR light. In one simulation utilizing a voxel-based forward imaging model of the embodiment the simulation voxel volume was 16×16×50 voxels which correlates to a physical size value of about 1.2 cm×1.2 cm×0.5 cm (where chromophores were simulated up to the depth of 0.5 cm for a surface imaging area of 1.2 cm×1.2 cm). The number of voxels and dimensions can be varied and set with respect to physical dimensions of the sensor instrumentation and therefore can vary greatly in further embodiments of the present invention with respect to the example herein.

Figure 9:
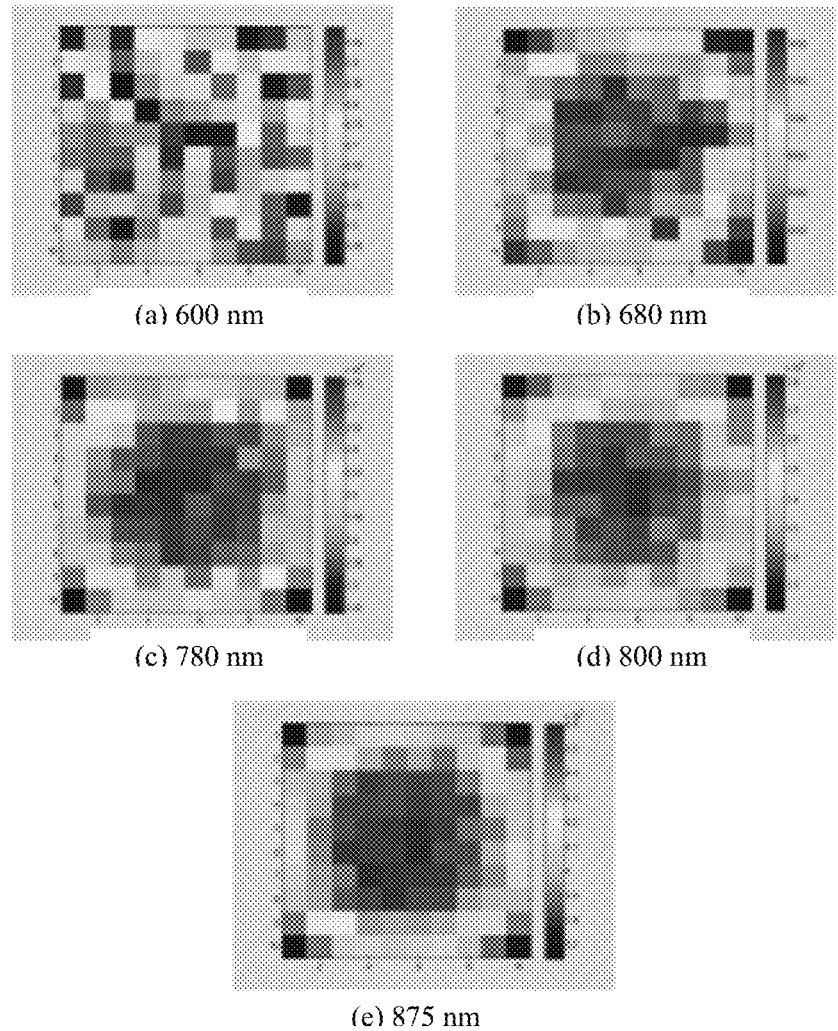
FIG. 9 demonstrates the transmission simulation images of melanin, blood, and glucose.

The embodiment was illuminated with a uniform square light source of about 1.2 cm×1.2 cm with a normal angle photon entry into the voxel volume. Illumination wavelengths utilized with respect to this exemplary embodiment included 600 nm, 680, nm, 780 nm, 800 nm, 875 nm, 910 nm and 980 nm. FIG. 9, for example, depicts exemplary embodiments of illumination wavelengths of 600 nm, 680 nm, 780 nm, 800 nm, and 875 nm, according to aspects of the present disclosure. The embodiment also used a transmission detector of 100 pixels over 0.75 $cm^2$ with 100 million photons per wavelength. In further embodiments of the present invention the pixel size range can be from about 2 mm×2 mm to about 1 cm×1 cm.

The pixel intensity in the transmission image is assumed dependent on the total absorption coefficient of the volume:

$$I/I_0 = f(\mu_a)$$

In the embodiment, based on simulation at 780 nm, the relation equation may take the form:

$$I/I_0 = \exp(-0.6316\sqrt{1.161\mu_a^2 + 9.503\mu_a})$$

In the embodiment a linear mixing model was assumed like so:

$$\mu_a(\lambda) = C_M\mu_a^{melanin}(\lambda) + C_B\mu_a^{blood}(\lambda) + (1 - C_M - C_B)\mu_a^{baseline}(\lambda)$$

where $$\mu_a^{blood}(\lambda) = [HbO_2]\mu_a^{HbO_2}(\lambda) + [Hb]\mu_a^{Hb}(\lambda) + [Glucose]\mu_a^{Glucose}(\lambda)$$

and $\mu_a^{Glucose}(\lambda)$ is measured experimentally for a concentration of 1 mg/dL in water. Therefore, a glucose concentration value for the embodiment of 100% would correspond to 1 mg/dL:

where Oxygen saturation may be calculated by the following equation:

$$[SO_2] = \frac{[HbO_2]}{[HbO_2] + [Hb]}$$

was assumed to be 75% for the embodiment. The melanin concentration ($C_M$), Blood concentration ($C_b$), and glucose concentration ([Glucose]) are left as unknown variables, as depicted, for example, in FIG. 10.

An estimation of glucose measurements in the simulated phantom using the volume model, substance true volume concentrations of melanin (1%), blood Hb (30%), oxygen saturation in HbO2 (75%), and glucose (100%) using the first wavelength set-1 as an example (embodiment) of 600, 680, 780, 800, 875 nm. The results are shown in FIG. 10. In the table, CM is the fraction volume for melanin (1%), CB is the fraction volume of total blood (Hb+HbO2), and Glucose is 100% with a regular concentration of 140 mg dL. The results of estimation of these substances in the simulated phantom using this set −1 are presented in the second column of the table as an example. The third shows the improvement in results using the preferred wavelength set−2 that includes 600 nm, 710 nm, 760 nm, 800 nm, 875 nm, 910 nm and 980 nm that resulted in better estimation.

A simulated volume, with true parameters Cm=1% Cb=30% and [Glucose]=100%, was simulated by Monte Carlo simulation to produce a set of multispectral transmission images. The pixel values in these images were averaged to a single number. The average pixel intensity number was converted to an absorption coefficient value.

In one embodiment of the present invention a linear array of LEDs at wavelengths including 600 nm, 710, nm, 760 nm, 800 nm, 875 nm, 910 nm and 980 nm are utilized. In the embodiment illumination is completed with a small angle divergent beam or a regular collimated beam and there is alignment with spatially distributed sensors to detect diffused transmittance. The embodiment also embraces drivers and pre-amplifiers. The synchronized control data acquisition system of this embodiment can be stand alone, synchronized with pulse rate, and synchronized with external programmed mode. Data collected from detector while the source is illuminated can be synchronized at an adaptable sampling rate for the embodiment. That means that data can be collected at regular interval with a sampling rate of 1 Hz to 100 KHz depending on the data acquisition electronics and storage system, and the requirement of the data processing algorithm. For example, once the pulse rate through oximetry is determined, the data can be sampled at the heart rate including systolic and diastolic events to compare the increase of absorption in the increased blood volume between diastole and systole of the heart cycle.

In one embodiment of the present invention an optical device with a linear array or circular co-axial cable based module of multispectral LED sources aligned with sensors first demonstrates pulse oximetry to provide reference of pulse rate and relative oxygen level. In the embodiment the pulse rate is used to tag the measurements to estimate the increase in blood glucose with the increased volume of blood in the tissue. Sampled data is then analyzed through un-mixing model based analysis of multiple measurements taken at selected wavelengths during the diastole and systole of the heart cycle.

Figure 11:
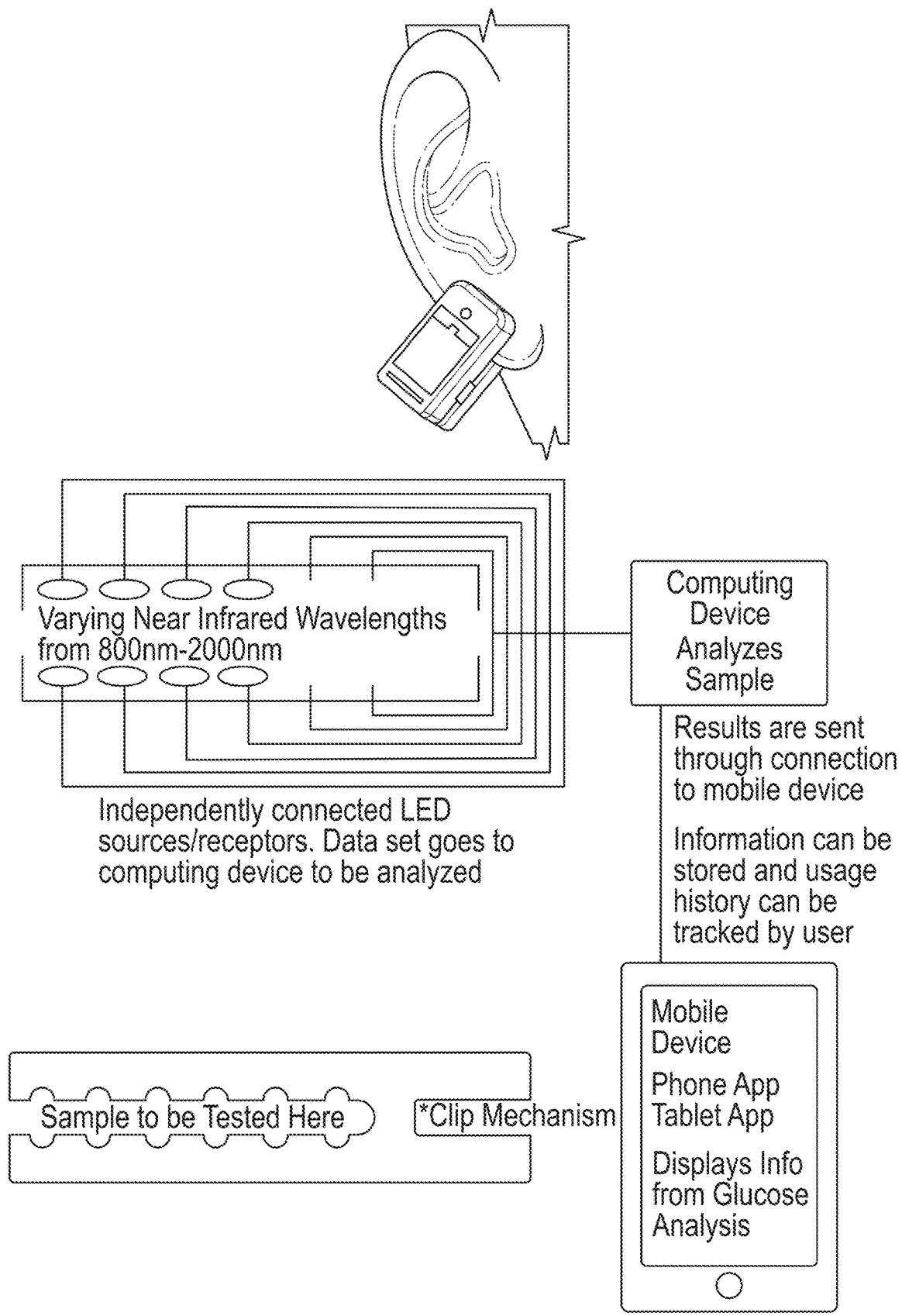
FIG. 11 displays schematically one embodiment of the present invention.

FIG. 11 shows a systematic diagram of an embodiment of the system showing on left a subject wearing a linear source-detector array based sensor clip at the earlobe, according to some aspects of the present disclosure. In this embodiment, each source is tuned at a specific individual wavelength. The clip is shown in the black figure at the bottom where the earlobe is to be placed in the middle cavity. Major parts of the embodiment are shown on the right including the linear array source-detector based sensor system, a computer-chip processor used for data acquisition, sampling and analysis, and a smart mobile device to store and display the data and associated analysis for monitoring, diagnosis and therapeutic intervention purposes.

Figure 12:
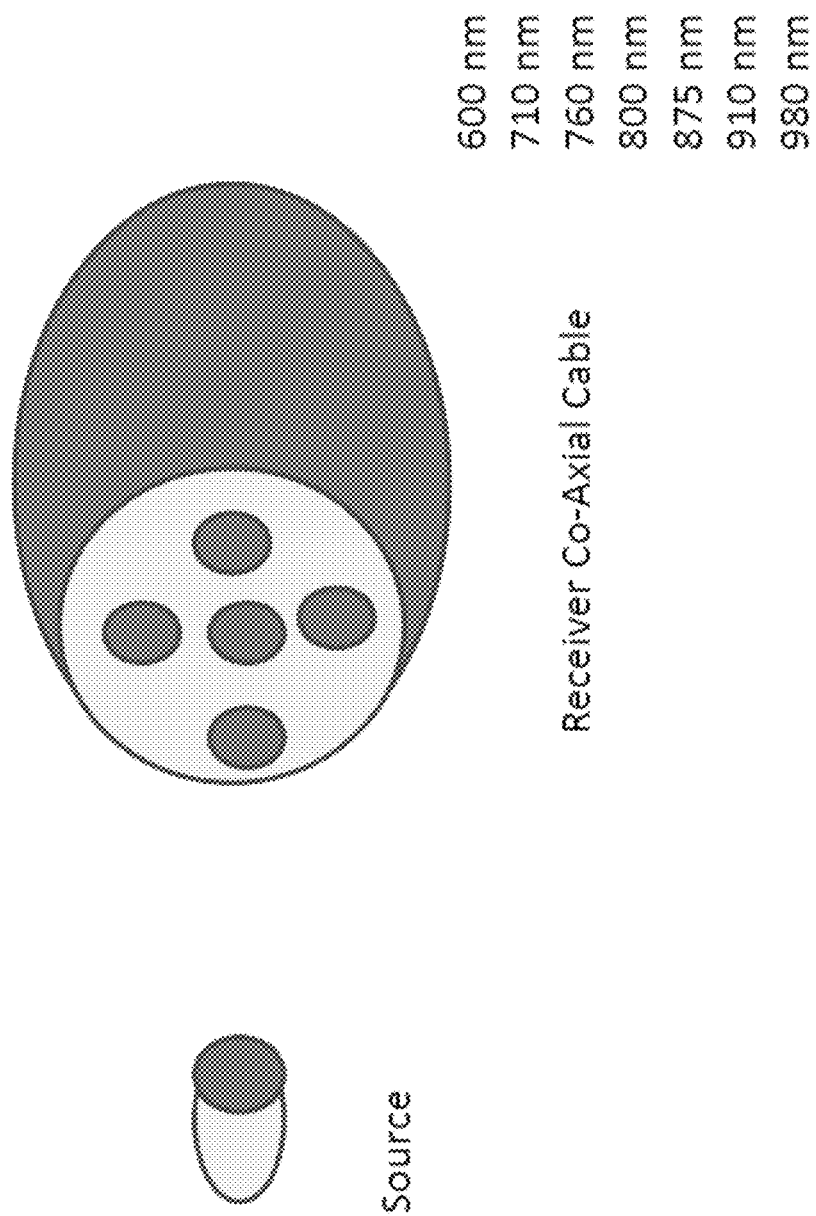
FIG. 12 illustrates shows a single-source (multiplexed)-co-ax receiver.

FIG. 12 shows an alternate embodiment of the co-axial sensor-detector array where a single source is modulated to provide different wavelength beams at sequential time-slots (on the left). Various co-axial detectors tuned at different wavelengths are circularly rotated and aligned to radiation beam for scanning the tissue for measurements.

Figure 13:
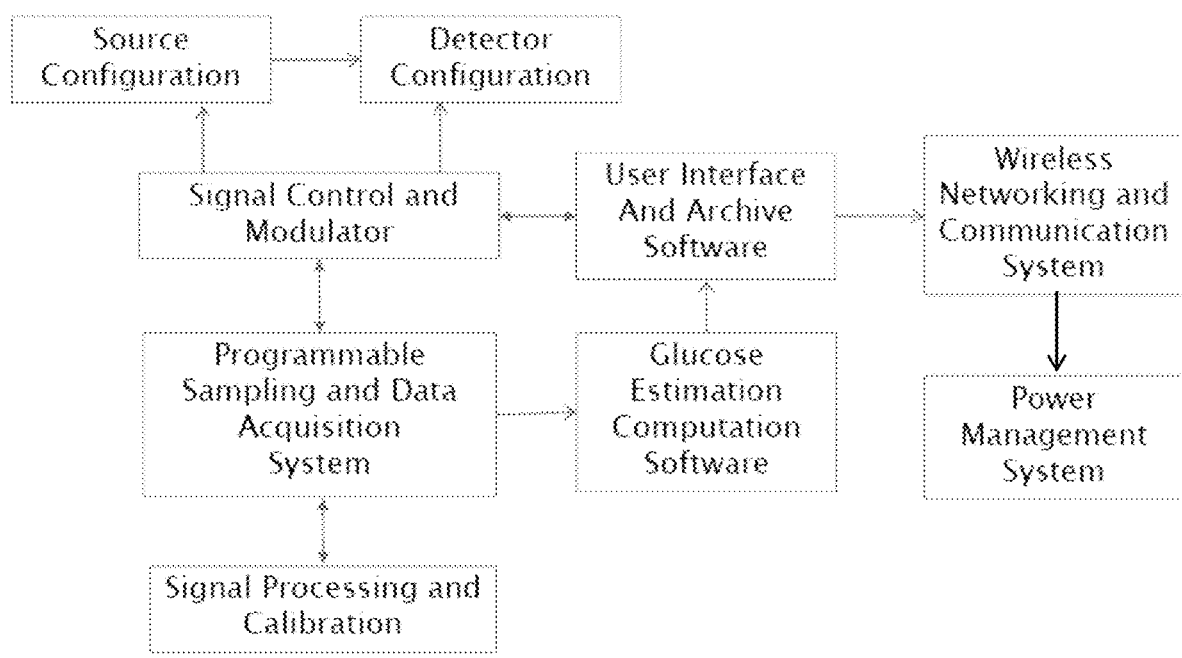
FIG. 13 depicts system level configuration of one embodiment of the present invention.

FIG. 13 illustrates an exemplary system level configuration according to some aspects of the present disclosure. In the exemplary embodiment, the system level configuration may comprise a source and detector configuration as depicted. In some examples, a user interface may be employed. A wireless networking and communication system, along with estimation computation software to estimate glucose concentration in the blood, may be used to relay glucose estimation results to the user via the user interface (e.g., a smart phone, tablet, etc.).

In the embodiment the raw signals are processed through a convolution function representing the degradation of the signal caused by physical illuminators and sensor coupling response transfer functions. Once the initial estimate of oxygen is determined (using well-known pulse oximetry method, the glucose is estimated by solving the mixing model equation using the successive measurements taken at pulse rate (with diastole and systole time tags) for increased blood volume in the tissue. The optimization of glucose estimation from the mixing model can be performed using the known optimization methods such as genetic algorithms.

While the initial glucose estimate from the above mixing equation provides a good "first guess", the solution obtained may not be optimal and can be further improved through known optimization methods such as, but not limited to the genetic algorithm (GA) optimization method (L. Davis, Handbook of Genetic Algorithms. New York: Van Nostrand Reinhold, 1991)

The GA optimization begins by initializing a population of initial and candidate solutions. Each candidate solution is encoded as a "chromosome" for use during the GA. The chromosome for one particular individual in the population is defined by the melanin, blood, and glucose concentrations. For example, the chromosome for the initial volume estimate (henceforth known as the model chromosome) is defined as the set:

$$\{\mu_a^{melanin}, \mu_a^{Hb}, \mu_a^{Hbo_2}, \mu_a^{glucose}\}$$

The values in each chromosome, known as alleles, represent the average concentration distributed in the tissue of the respective chromophores, melanin, hemoglobin, oxygenated hemoglobin (or total blood as the combined value) and glucose over the voxels for which data is collected for the embodiment. To further improve the estimation of distribution of chromophores over the imaged area (voxels), members of the GA population are varied around the model chromosome according to three concentric categories, circular areas around the center where the source and central detector pair is aligned. This is defined as red central space. The surrounding circular area of detector space shown in yellow belongs to second category and detector space in green represents the third category for weighting the illumination scattering effect or spread of beam in the tissue.

For the no bias category, the weights used in GA optimization are assigned from the Monet-Carlo simulation results. For example, in certain embodiments of the present invention they could be 50%, 30%, and 20%, respectively. For the shallow bias category of certain embodiments of the present invention, each allele has a 15% chance of decreasing by 10% (meaning the diffusion is stronger giving less weight to the data collected in central (red) zone), an 80% of not changing, and a 5% chance of increasing by 10% (meaning that diffusion is weaker to give more weight to the data collected in central detector space). The weights in remaining surrounding areas are adjusted accordingly for normalization to 100% total. For example it could change from 50-30-20 to 40-30-30 depending on the embodiment and conditions. Stronger or weaker biases could be created depending on the type of skin, e.g. stronger for darker (more amount of melanin) and weaker for lighter skin (less amount of melanin). In this manner, population variability is maintained, but each chromosome is based on the initial chromosome representing initial distribution obtained from the mixing equation solution.

GA requires formulation of a fitness function to evaluate the goodness of each possible solution based on the chromosome variations. Chromosomes are evaluated as to their fitness by executing the forward model on the chromosome (computing the distribution of absorption data using the estimated chromophore values in the Monte-Carlo model), and then comparing it with the real detector data acquired from the tissue for a particular embodiment of the present invention. The fitness F of each chromosome is then evaluated by a comparison between the multispectral images of the tissue ($I_\lambda^{real}$) and the images generated by the forward model simulation ($I_\lambda$) on that chromosome, within the defined mask of bias category distribution as defined above:

$$F = -\ln\left(\frac{1}{N_\lambda N_\ell}\sum_{\lambda,x,y}\frac{|I_\lambda(x,y) - I_\lambda^{real}(x,y)|}{I_\lambda^{real}(x,y)}m(x,y)\right)$$

where $N_\lambda$ is the number of wavelengths used for imaging, and $N_l$ is the number of data points within the mask such that $N_l = \Sigma_{x,y} m(x,y)$.

For the embodiment the calibration is performed through a look up table with respect to oximetry measurements that is normalized through ratiometric comparative measurements of pulse oximetry at 600 and 910 nm as it will remove the melanin and other absorption variables in the mixing model.

Experimental

The absorption per wave length was determined for 132 phantom samples and 132 simulated samples at various levels of glucose concentration at different wavelengths.

Figure 14A:
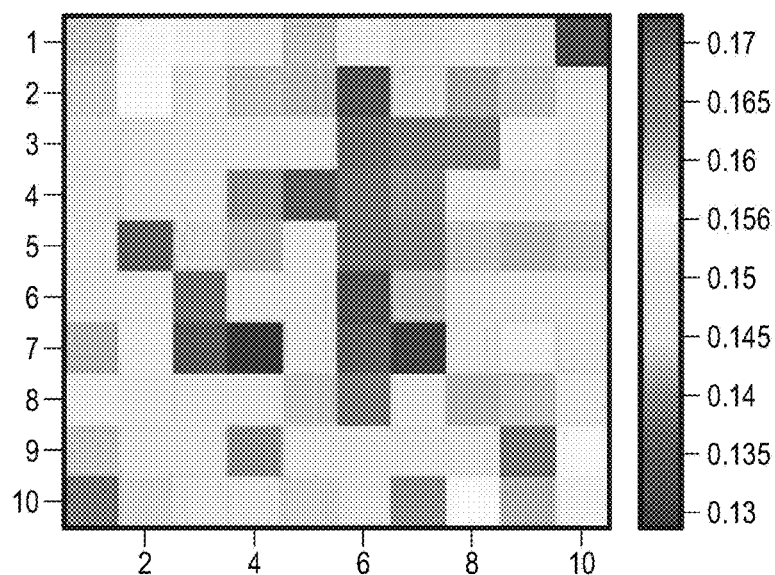
FIGS. 14A-14C show simulated versus tube phantom.
Figure 14B:
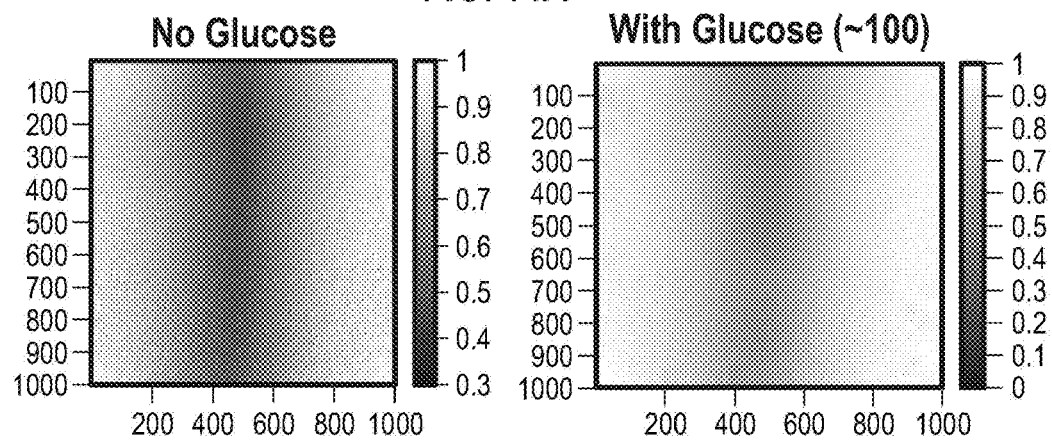
Figure 14C:
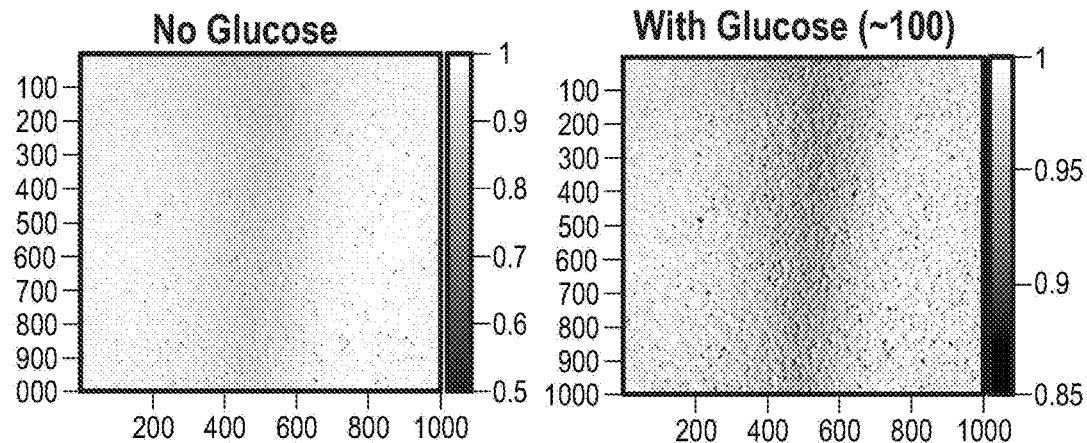

FIGS. 14A-14C show Simulation versus Tube Phantom. On the left is a simulated tissue image from Monte-Carlo simulation at the regular glucose level of 140 mg/dL. On the right are images of the physical tube-phantom taking from a multi-spectral CCD camera with no glucose and 100% glucose volume in the embedded tube in the middle for two example wavelengths: 680 nm (FIG. 14B) and 875 nm (FIG. 14C).

The measurements shown in FIGS. 15A-15F are used in the glucose estimation using the described model.
Simulation Volume Model
10×10 pixels
Transmission Detector: 10×10 pixels, for an overall physical detector area of 0.75 cm2
Voxel volume: 16×16×50 voxels, of physical size 1.2 cm×1.2 cm×0.5 cm
  2×16×2 voxel, of physical size 0.15 cm×16 cm×0.15 cm, tube embedded in center of volume
Illumination: A uniform square light source, 1.2 cm×1.2 cm (covering the entire volume), with a perpendicular entry angle for photons.
Wavelengths available: 600, 680, 780, 800, 875 nm
100 million photos simulated per wavelength
Melanin concentration=1%
Blood concentration=30%
SO2 concentration=75%

| Glucose concentration = | |
| --- | --- |
| | Experiment |
| Danger Low | 20 mg/dL |
| Low | 60 mg/dL |
| Fasting | 100 mg/dL |
| Regular | 140 mg/dL |
| High | 200 mg/dL |
| Danger High | 500 mg/dL |

Linear mixing model assumed:

$$\mu_a(\lambda) = C_M \mu_a^{melanin}(\lambda) + C_B \mu_a^{blood}(\lambda) + (1 - C_M - C_B)\mu_a^{baseline}(\lambda)$$

where $$\mu_a^{blood}(\lambda) = [HbO_2]\mu_a^{HbO_2}(\lambda) + [Hb]\mu_a^{Hb}(\lambda) + [Glucose]\mu_a^{Glucose}(\lambda)$$

The results are shown in FIGS. 15A-E.

Although the systems and methods of the present disclosure have been described with reference to exemplary embodiments thereof, the present disclosure is not limited thereby. Indeed, the exemplary embodiments are implementations of the disclosed systems and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

The invention claimed is:

1. A method of monitoring blood concentration of a substance comprising:
  illuminating a specified location of a subject a first time with one or more light sources using near infrared spectroscopy, wherein a wavelength of the one or more light sources is in the range of 600 nm to 1,000 nm;
  detecting, via one or more linear source-detector array sensors aligned with the one or more light sources, initial absorption data and pulse oximetry information in response to illumination of the specified location the first time;

sampling the initial absorption data, via one or more processors, at a first sampling rate, wherein the initial absorption data relates to one or more absorption coefficients, and wherein the initial absorption data is sampled over a heart cycle event;

illuminating the specified location of the subject a second time with the one or more light sources using near infrared spectroscopy in the range of 600 nm to 1,000 nm;

detecting a second set of absorption data in response to illumination of the specified location the second time;

sampling the second set of absorption data, at a second sampling rate, via the one or more processors, wherein the second sampling rate is lower than the first sampling rate, and wherein the second set of absorption data relates to the one or more absorption coefficients;

adjusting, via the one or more processors, at least the second set of absorption data based on a convolution function, wherein the adjusted second set of absorption data comprises at least a melanin skin absorption coefficient, a blood skin absorption coefficient, and a baseline skin absorption coefficient; and estimating a level of the substance in the blood based at least in part on:
  the pulse oximetry information, and a mixing model equation, wherein the mixing model equation is based at least in part on a sum of:
    a product of the melanin skin absorption coefficient and a melanin concentration associated with the melanin skin absorption coefficient,
    a product of the blood skin absorption coefficient and a blood concentration associated with the blood skin absorption coefficient, and
    a product of the baseline skin absorption coefficient and a baseline skin concentration, wherein:
      the baseline skin concentration is a difference between one and the sum of the melanin concentration and the blood concentration, and
      the baseline skin absorption coefficient is based at least in part on a natural exponential function of the wavelength; and
  a genetic algorithm chromosome associated with a concentration of the substance in a tissue beneath the specified location, that is utilized to obtain a final reading for the estimate.

2. The method of claim 1, which is non-invasive to the subject whose blood is being analyzed.

3. The method of claim 1, wherein the substance is glucose, glycolated hemoglobin or cholesterol.

4. The method of claim 1, wherein the initial absorption data is measured over a period of time to analyze possible temporal variations.

5. The method of claim 1, wherein the heart cycle event is a systolic and/or a diastolic event.

6. The method of claim 1, further comprising adjusting the initial absorption data and the second set of absorption data by applying a Monte Carlo simulation to the initial absorption data and the second set of absorption data, wherein the Monte Carlo simulation is a voxel-based forward imaging model of a surface area of skin on which the initial absorption data and the second set of absorption data is measured.

7. The method of claim 1, wherein the one or more absorption coefficients are oxygenated hemoglobin and deoxygenated hemoglobin.

8. The method of claim 1, wherein the mixing model equation is a linear mixing model equation, and wherein the blood concentration of the substance is calculated using oxygen saturation.

9. The method of claim 1, wherein the initial absorption data and second set of absorption data are measured from a surface area of skin of the subject.

10. The method of claim 1, wherein a surface area of skin of the subject is an ear lobe.

11. The method of claim 1, wherein the final reading is a final blood substance reading that is based at least in part on a distribution of chromophores in the blood corresponding to a plurality of concentric circular areas in a tissue illuminated by the one or more light sources in the specified area location.

12. The method of claim 1, wherein the baseline skin absorption coefficient is further based at least in part on the natural exponential function of a first constant subtracted from the wavelength, and divided by a second constant.

13. A method of monitoring blood concentration of glucose comprising:
  sampling initial absorption data, via one or more processors, at a first sampling rate in response to:
    illuminating skin of a subject using one or more light sources, and
    detecting the initial absorption data, using one or more near infrared spectroscopy (NIR) linear source-detector array sensors aligned with the one or more light sources, wherein:
      a wavelength of the one or more light sources is in the range of 600 nm to 1,000 nm,
      the initial absorption data relates to one or more absorption coefficients, and
      the initial absorption data is sampled over a heart cycle event;
  sampling a second set of absorption data at a second sampling rate, via the one or more processors, in response to illuminating the skin of the subject using near infrared spectroscopy (NIR) in the range of 600 nm to 1,000 nm, wherein the second sampling rate is lower than the first sampling rate, and wherein the second set of absorption data relates to the one or more absorption coefficients;
  adjusting, via the one or more processors, at least the second set of absorption data by applying a convolution function, wherein the adjusted second set of absorption data comprises at least a melanin skin absorption coefficient, a blood skin absorption coefficient, and a baseline skin absorption coefficient; and
  estimating a level of the glucose in the blood based at least in part on:
    pulse oximetry information, and a mixing model equation, wherein the mixing model equation is based at least in part on a sum of:
      a product of the melanin skin absorption coefficient and a melanin concentration associated with the melanin skin absorption coefficient,
      a product of the blood skin absorption coefficient and a blood concentration associated with the blood skin absorption coefficient, and
      a product of the baseline skin absorption coefficient and a baseline skin concentration, wherein:
        the baseline skin concentration is a difference between one and the sum of the melanin concentration and the blood concentration; and the baseline skin absorption coefficient is based at least in part on a natural exponential function of the wavelength; and a genetic algorithm chromosome associated with a concentration of the glucose in a tissue beneath a specified location, that is utilized to obtain a final reading for the estimate.

14. The method of claim 13, which is non-invasive to the subject whose blood is being analyzed.

15. The method of claim 13, wherein the initial absorption data is measured over a period of time to analyze possible temporal variations while also providing time tag information for systolic and diastolic events.

16. The method of claim 13, wherein the heart cycle event is a systolic and/or a diastolic event.

17. The method of claim 13, further comprising adjusting the initial absorption data and the second set of absorption data by applying a Monte Carlo simulation to the initial absorption data and the second set of absorption data, wherein the Monte Carlo simulation is a voxel-based forward imaging model of a surface area of the skin on which the initial absorption data and the second set of absorption data is measured.

18. The method of claim 13, wherein the one or more absorption coefficients are oxygenated hemoglobin and deoxygenated hemoglobin.

19. The method of claim 13, wherein the mixing model equation is a linear mixing model equation, and wherein the blood concentration of the glucose is calculated using oxygen saturation.

20. The method of claim 13, wherein the initial absorption data and second set of absorption data are measured from a surface area of the skin of the subject.

21. The method of claim 13, wherein the final reading is a final blood glucose reading that is based at least in part on a distribution of chromophores in the blood corresponding to a plurality of concentric circular areas in a tissue illuminated by the one or more light sources in the specified location.

* * * * *